United States Patent [19]
Sangokoya et al.

[11] Patent Number: 5,847,177
[45] Date of Patent: Dec. 8, 1998

[54] PRODUCTION OF HYDROCARBON-SOLUBLE HYDROCARBYLALUMINOXANES

[75] Inventors: Samuel A. Sangokoya; Karl E. Wiegand, both of Baton Rouge, La.

[73] Assignee: Albemarle Corporation, Richmond, Va.

[21] Appl. No.: 729,268

[22] Filed: Oct. 10, 1996

[51] Int. Cl.⁶ ..................................................... C07F 5/06
[52] U.S. Cl. .......................... 556/179; 502/111; 502/117; 502/152
[58] Field of Search .............................. 556/179; 502/111, 502/117, 152

[56] References Cited

U.S. PATENT DOCUMENTS

| | | | |
|---|---|---|---|
| 3,657,159 | 4/1972 | Vandenberg et al. | 260/2 |
| 3,740,384 | 6/1973 | Ballard et al. | 260/94.9 |
| 3,969,332 | 7/1976 | Gloriod et al. | 526/128 |
| 4,931,517 | 6/1990 | Fujita | 526/128 |
| 4,945,076 | 7/1990 | Piotrowski et al. | 502/117 |
| 4,960,878 | 10/1990 | Crapo et al. | 556/179 |
| 5,017,714 | 5/1991 | Welborn | 556/12 |
| 5,026,798 | 6/1991 | Canich | 526/127 |
| 5,034,549 | 7/1991 | Piotrowski et al. | 556/10 |
| 5,041,584 | 8/1991 | Crapo et al. | 556/179 |
| 5,057,475 | 10/1991 | Canich et al. | 502/104 |
| 5,061,668 | 10/1991 | Hoxmeier et al. | 502/117 |
| 5,066,631 | 11/1991 | Sangokoya et al. | 502/152 |
| 5,086,024 | 2/1992 | Crapo et al. | 502/117 |
| 5,122,491 | 6/1992 | Kioka et al. | 502/117 |
| 5,329,032 | 7/1994 | Tran et al. | 556/179 |
| 5,371,260 | 12/1994 | Sangokoya | 556/171 |
| 5,391,529 | 2/1995 | Sangokoya | 502/103 |

FOREIGN PATENT DOCUMENTS

| | | |
|---|---|---|
| 2112965 | 8/1994 | Canada . |
| 0129368 | 5/1984 | European Pat. Off. . |
| 0367503 | 10/1989 | European Pat. Off. . |
| 0418937 | 7/1990 | European Pat. Off. . |
| 0561476 | 3/1993 | European Pat. Off. . |
| 0621279 | 1/1994 | European Pat. Off. . |
| 1-258686 | 10/1989 | Japan . |

OTHER PUBLICATIONS

Siloxy–substituted Alumoxanes:Synthesis from Polydialkylsiloxanes and Trimethylaluminium, and Application as Aluminosilicate Precursors, J. Mater. Chem., 1993, pp. 597–602.

Ceram. Trans., 19 (Adv. Composite Matter)) pp. 35–41 (1991), "Design and Synthesis of Polymeric Precursors to Aluminosilicates", by Allen W. Apblett, et al. (no month available).

Primary Examiner—Porfirio Nazario-Gonzalez
Attorney, Agent, or Firm—Philip M. Pippenger

[57] ABSTRACT

Novel aluminum-containing compositions having increased paraffin-solubility are produced from a methylaluminoxane composition having lower paraffin-solubility. These compositions are formed by mixing in liquid phase (A) at least one aluminum trialkyl (or solution or suspension formed therefrom), where the aluminum trialkyl has at least 30 carbon atoms in the molecule, where each alkyl group thereof is bifurcated in the 2-position into a pair of branches, where one such branch has n carbon atoms and the other such branch has at least n+2 carbon atoms, and where n is at least 3; and (B) at least one methylaluminoxane composition having lower heptane-solubility (or a solution or slurry formed therefrom). Preferably, the resultant mixture is agitated at one or more elevated temperatures at which the mixture becomes even more homogeneous. The aluminum trialkyl preferably is one or more in which there are at least 36 carbon atoms in the molecule, in which n is at least 4 and in which the longer branch of the bifurcated alkyl groups has n+2 carbon atoms.

31 Claims, No Drawings

PRODUCTION OF HYDROCARBON-SOLUBLE HYDROCARBYLALUMINOXANES

TECHNICAL FIELD

This invention relates to production of hydrocarbylaluminoxane compositions that have improved solubility in liquid paraffinic hydrocarbons. More particularly, this invention relates to converting methylaluminoxane compositions that have low solubility in hydrocarbon solvents, especially in paraffinic hydrocarbon solvents, into aluminoxane compositions that have improved solubility in such solvents, without extensively modifying the fundamental organometallic character of the methylaluminoxane composition.

In the ensuing description and in the claims hereof, reference is sometimes made to solubility in heptane (i.e., n-heptane), because heptane is a typical, representative paraffinic hydrocarbon which serves as a very convenient point of reference for comparisons of solubility. However, such references to heptane do not constitute a limitation or restriction on the scope of this invention as the invention produces aluminoxane compositions that have improved solubility in a variety of liquid paraffinic hydrocarbons as compared to the solubility of the original methylaluminoxane in the same respective hydrocarbons.

BACKGROUND

Heretofore efforts have been made to improve the solubility and shelf-life stability of paraffinic solutions of methylaluminoxanes. Among published activities along these lines are U.S. Pat. Nos. 4,960,878; 5,041,584; 5,066,631; 5,086,024; and Japan Kokai No. 1-258,686 (laid open Oct. 16, 1989).

Further improvements in this regard would constitute a meritorious contribution to the art. This invention is deemed to provide such a contribution.

THE INVENTION

This invention provides, inter alia, a process of producing an aluminum-containing composition having increased solubility in liquid paraffins exemplified by heptane, where the aluminum-containing composition is formed from a methylaluminoxane having lower heptane-solubility. The process comprises mixing in liquid phase:

A) at least one aluminum trialkyl or a solution or suspension formed therefrom, wherein the aluminum trialkyl has at least 30 carbon atoms in the molecule, wherein each alkyl group of the aluminum trialkyl is bifurcated in the 2-position into a pair of branches, preferably linear branches, wherein one said branch has n carbon atoms and the other said branch has at least n+2 carbon atoms, and wherein n is at least 3, and B) at least one such methylaluminoxane composition having lower heptane-solubility, or a solution or slurry formed therefrom.

In conducting this operation B) is preferably in the form of a solution, typically in a liquid aromatic hydrocarbon medium, and preferably in a liquid, mononuclear aromatic hydrocarbon medium. Such solution may be, but need not be, visually hazy, and it malt even contain a solids phase of inherent organoaluminum material. While the order of addition or mixing is not critical, it is preferable to add A) to B) and, in any event, to agitate the resulting mixture to ensure thorough mixing.

It is also preferred to heat the agitated mixture at one or more temperatures (e.g., in the range of about 30° to about 100° C.) at which the mixture becomes even more homogeneous.

In other embodiments of the invention, the aluminum-containing composition having increased heptane-solubility is recovered by removing the solvent from the mixture after such aluminum-containing composition has been formed. This can be accomplished by distilling off the hydrocarbon solvent, preferably at reduced pressure At this point an oily or waxy solid product results instead of the usual solid product produced when removing solvent from methylaluminoxane by distillation at reduced pressure. Still other embodiments of the invention involve mixing at least a portion of such recovered aluminum-containing composition with a liquid paraffinic or cycloparaffinic hydrocarbon solvent.

The above operations should of course be conducted in an appropriate inert environment such as in an atmosphere of dry inert gas (e.g., nitrogen, argon, neon, krypton, etc.).

The practice of this invention results in a change in the composition of the original methylaluminoxane into a new composition. The exact nature of the transformation(s) occurring in the process are not known with certainty, but may involve at least in part, alkyl exchange and/or complex formation.

Preferred aluminum trialkyls for use in the process have at least 30 carbon atoms in the molecule, and n, the above number of carbon atoms in the smaller branch, is at least 4. Particularly preferred aluminum trialkyls are those wherein there are at least 36 carbon atoms in the molecule, wherein n is at least 4 and wherein the longer branch of each bifurcated alkyl group has n+2 carbon atoms. Preferred examples include tris(2-butyloctyl)aluminum, tris(2-butyldecyl)aluminum, tris(2-pentylnonyl)aluminum, tris(2-hexyldecyl)aluminum, tris(2-hexyldodecyl)aluminum, tris(2-heptylundecyl)aluminum, tris(2-octyldodecyl)aluminum, tris(2-octyltetradecyl)aluminum, tris(2-nonyltridecyl)aluminum, and tris(2-decyltetradecyl)aluminum, tris(2-decylhexadecyl)aluminum, as well as any combination of any two or more of the foregoing aluminum trialkyls.

Methylaluminoxane may exit in the form of a linear or cyclic polymer with the simplest component being tetramethylaluminoxane, $(CH_3)_2AlOAl(CH_3)_2$. The compounds preferred for use in olefin polymerization usually contain about 5 to 20 of the repeating units:

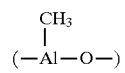

The aluminoxane compounds can be made, as is known in the art, by partial hydrolysis of trimethylaluminum which is slurried or dissolved in an organic solvent such as toluene and treated under suitably controlled conditions with free water or a hydrated compound. The resulting methylaluminoxane product is usually a mixture of methyl aluminoxane and trimethylaluminum. The product is typically a solid which can be recovered from the reaction mixture by removal of the solvent.

The amount of the above aluminum trialkyls which is effective to solubilize the methylaluminoxane will depend upon the particular aluminum trialkyl compound used. Generally, in aliphatic solvents from about 0.5 to 20 and preferably 1.0 to 10 moles of methylaluminoxane, calculated from the neat methylaluminoxane content of the methylaluminoxane product to be dissolved, can be solubilized per mole of aluminum trialkyl (mole ratio of aluminum as aluminoxane to aluminum as aluminum trialkyl of about 0.5:1 to 20:1). In aromatic solvents from about 1 to 35 moles of methylaluminoxane can be solubilized per mole of the aluminum trialkyl.

Aliphatic hydrocarbons which can be used as solvents include, for example, pentane, hexane, 2-methylpentane, 3-methylpentane, heptane, 2,2-dimethylpentane, 2,3-dimethylpentane, 2,4-dimethylpentane, 3,3-dimethylpentane, 3-ethylpentane, 2-methylhexane, 3-methylhexane, octane, 2-methylheptane, 4-methylheptane, 2,3-dimethylhexane, 2,4-dimethylhexane, 2,5-dimethylhexane, 3,4-dimethylhexane, 3-ethylhexane, 2,2,4-tri-methylpentane, 3-ethyl-2-methylpentane, nonane, 2,6-dimethylheptane, decane, dodecane, tetradecane, petroleum ether, and like liquid paraffinic hydrocarbons, with those having from 5 to 10 carbon atoms being preferred. Cycloaliphatics such as cyclohexane, methylcyclopentane, methylcyclohexane, cycloheptane, and like liquid cyclic saturated hydrocarbons can be used. Aromatic hydrocarbons which can be used as solvents include benzene, toluene, xylene, cumene, tetralin, and similar liquid aromatic hydrocarbon solvents, with those having from 6 to about 12 carbon atoms being preferred.

The concentration of methylaluminoxane in the solutions of the invention can vary and in aromatic solvents generally ranges from about 5 to 30 weight percent of aluminum as methylaluminoxane product, based on the total weight of solution, and from about 5 to 15 weight percent in aliphatic solvents. Of this amount up to about 70 mol percent of the aluminum, and usually about 25 to 30 mol percent, may be present as trimethylaluminum.

In order to illustrate the practice and advantages of this invention the following non-limiting examples are presented. The operations described in the examples were carried out under inert atmospheric conditions using Schlenk glassware and vacuum line in conjunction with a nitrogen-drybox. Solvents were distilled using standard method. Filtration and vacuum distillation were done inside a nitrogen-drybox and distillates were collected in a trap at −78° C. Methylaluminoxane (MAO) was obtained from stock solutions produced and marketed by Albemarle Corporation. It is to be understood that this invention is not to be limited to the specific details set forth in these examples.

EXAMPLE 1

Preparation of tris(2-hexyldecyl)aluminum

2-Hexyl-1-decene (336 g, 1.5 mL) was placed in a 2-liter three necked reaction flask equipped with condenser and magnetic stirrer. Triisobutylaluminum (TIBA, 100 g, 0.5 mol) was added in the drybox. The apparatus was then set up in a well vented hood. Under nitrogen flow, the mixture was heated at 100° C. for 10 hours. Thereafter, the mixture was further heated at 120° C. for another 10 hours. Dissolved volatiles were removed under reduced pressure to obtain 345 g of clear liquid product. Analysis showed over 97 percent yield based on TIBA.

EXAMPLE 2

Preparation of an Alkane-Soluble Aluminoxane Composition

A cloudy toluene solution of MAO (76 g, 387 mmol Al) was placed in a reaction bottle. Then tris(2-hexyldecyl) aluminum (14.3 g, 19.4 mmol Al, 5 mol %) was added. The mixture was stirred at room temperature for 3 hours and remained cloudy. On heating at 95° C. for 3 hours, a clear solution resulted. The mixture was filtered and then concentrated. Heptane (10 g) was added to the oil and then stirred at room temperature overnight. The resulting product was only slightly cloudy and was filtered through medium frit to obtain a clear solution. Analysis showed that 86% of the original aluminum value was recovered in the alkane-soluble aluminoxane composition of this invention.

EXAMPLE 3

Preparation of an Alkane-Soluble Aluminoxane Composition

Using the procedure as in Example 2, a cloudy MAO solution in toluene (73 g, 372 mmol Al) was treated with tris(2-hexyldecyl)aluminum (19.1 g, 26.1 mmol Al, 7 mol %) to obtain a clear solution. Thus the 7% treatment is more efficient compared to the 5% treatment of Example 2. The product was again concentrated to an oil and then treated with heptane to obtain after filtration a clear heptane-soluble aluminoxane composition of this invention. Analysis showed that 90% of the original aluminum value was recovered.

Examples 2 and 3 illustrate that aluminum trialkyls of the type used in the practice of this invention are capable in small concentrations of clarifying a cloudy methylaluminoxane (MAO) solution in toluene, and also producing alkane-soluble aluminoxane compositions after solvent exchange.

Ethylene polymerization results showed that as regards polymerization activity, the aluminoxane products of Examples 2 and 3 compared very well to the original solution of methylaluminoxane in toluene. Moreover, if the MAO is fresh and gel-free, the amount of aluminum triallyl required to achieve the advantages of this invention (e.g., 1–3 mol %) is substantially less than required when the MAO is old and contains gel.

The materials referred to by chemical name or formula anywhere in the specification or claims hereof are identified as ingredients to be brought together in connection with performing a desired reaction or operation, or in forming a mixture to be used in conducting a desired reaction or operation. Accordingly, even though the claims hereinafter may refer to substances in the present tense ("comprises", "is", etc.), the reference is to the substance, as it existed at the time just before it was first contacted, blended or mixed with one or more other substances in accordance with the present disclosure. The fact that a substance may lose its original identity through a preliminary chemical reaction, complex formation, salvation, or other transformation during the course of contacting, blending or mixing operations, if done in accordance with the disclosure hereof, is within the purview and scope of this invention.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process of producing an aluminum-containing composition having increased heptane-solubility from a methylaluminoxane composition having lower heptane-solubility, which process comprises mixing in liquid phase:

A) at least one aluminum trialkyl or a solution or suspension formed therefrom, wherein said aluminum trialkyl has at least 30 carbon atoms in the molecule, wherein each alkyl group of said aluminum trialkyl is bifurcated in the 2-position into a pair of branches, wherein one said branch has n carbon atoms and the other said branch has at least n+2 carbon atoms, and wherein n is at least 3, and B) at least one said methylaluminoxane composition having lower heptane-solubility or a solution or slurry formed therefrom.

2. A process according to claim 1 wherein B) is in the form of a solution which, optionally is visually hazy.

3. A process according to claim 1 wherein said at least one aluminum trialkyl has at least 36 carbon atoms in the molecule, and wherein n is at least 4.

4. A process according to claim 1 wherein said aluminum trialkyl is tris(2-butyloctyl)aluminum, tris(2-pentylnonyl) aluminum, tris(2-hexyldecyl)aluminum, tris(2-heptylundecyl)aluminum, tris(2-octyldodecyl)aluminum, tris(2-nonyltridecyl)aluminum, or tris(2-decyltetradecyl) aluminum, or a combination of any two or more of the foregoing aluminum trialkyls.

5. A process according to claim 1 wherein B) is a solution formed by dissolving or producing at least one methylaluminoxane composition in a liquid aromatic hydrocarbon medium.

6. A process according to claim 1 wherein B) is a solution formed by dissolving or producing at least one methylaluminoxane composition in a liquid mononuclear aromatic hydrocarbon medium.

7. A process according to claim 1 wherein A) is added to B) and the resulting mixture is agitated hydrocarbon medium.

8. A process according to claim 1 further comprising heating the mixture at one or more temperatures at which the mixture becomes more homogeneous.

9. A process according to claim 2 wherein A) is in neat form.

10. A process according to claim 2 further comprising recovering the aluminum-containing composition having increased heptane-solubility by removing the solvent from the mixture after said aluminum-containing composition has been formed.

11. A process according to claim 10 further comprising mixing at least a portion of the recovered aluminum-containing composition with a liquid paraffinic or cycloparaffinic hydrocarbon solvent.

12. A process of producing an aluminum-containing composition having increased heptane-solubility from a methylaluminoxane composition having lower heptane-solubility, which process comprises
1) mixing in liquid phase:
  A) at least one aluminum trialkyl or a solution or suspension formed therefrom, wherein said aluminum trialkyl has at least 30 carbon atoms in the molecule, wherein each alkyl group of said aluminum trialkyl is bifurcated in the 2-position into a pair of branches, wherein one said branch has n carbon atoms and the other said branch has at least n+2 carbon atoms, and wherein n is at least 3, and
  B) at least one such methylaluminoxane composition having lower heptane-solubility or a solution or slurry formed therefrom; and
2) agitating the resultant mixture at one or more elevated temperatures at which the mixture becomes more homogeneous.

13. A process according to claim 12 wherein B) is in the form of a solution which, optionally, is visually hazy.

14. A process according to claim 12 wherein said at least one aluminum trialkyl has at least 36 carbon atoms in the molecule, and wherein n is at least 4.

15. A process according to claim 12 wherein said aluminum trialkyl is tris(2-butyloctyl)aluminum, tris(2-pentylnonyl)aluminum, tris(2-hexyldecyl)aluminum, tris(2-heptylundecyl)aluminum, tris(2-octyldodecyl)aluminum, tris(2-nonyltridecyl)aluminum, or tris(2-decyltetradecyl) aluminum, or a combination of any two or more of the foregoing aluminum trialkyls.

16. A process according to claim 12 wherein B) is a solution formed by dissolving or producing at least one methylaluminoxane composition in a liquid aromatic hydrocarbon medium.

17. A process according to claim 12 wherein B) is a solution formed by dissolving or producing at least one methylaluminoxane composition in a liquid mononuclear aromatic hydrocarbon medium.

18. A process according to claim 12 wherein A) is in neat form.

19. A process according to claim 12 further comprising recovering the aluminum-containing composition having increased heptane-solubility by removing the solvent from the mixture after said aluminum-containing composition has been formed.

20. A process according to claim 19 further comprising mixing at least a portion of the recovered aluminum-containing composition with a liquid paraffinic or cycloparaffinic hydrocarbon solvent.

21. An aluminum-containing composition produced by a process according to claim 1.

22. An aluminum-containing composition produced by a process according to claim 3.

23. An aluminum-containing composition produced by a process according to claim 4.

24. An aluminum-containing composition produced by a process according to claim 10.

25. An aluminum-containing composition produced by a process according to claim 11.

26. A process according to claim 1 wherein said aluminum trialkyl is tris(2-hexyldecyl)aluminum.

27. A process according to claim 12 wherein said aluminum trialkyl is tris(2-hexyldecyl)aluminum.

28. An aluminum-containing composition produced by a process according to claim 26.

29. An aluminum-containing composition produced by a process according to claim 27.

30. A composition which comprises a liquid paraffinic or cycloparaffinic solvent containing a methylaluminoxane composition formed by mixing in an inert liquid phase (i) methylaluminoxane and (ii) tris(2-butyloctyl)aluminum, tris (2-pentylnonyl)aluminum, tris(2-hexyldecyl)aluminum, tris (2-heptylundecyl)aluminum, tris(2-octyldodecyl)aluminum, tris(2-nonyltridecyl)aluminum, or tris(2-decyltetradecyl) aluminum, or a combination of any two or more of the foregoing aluminum trialkyls.

31. A composition according to claim 30 wherein (ii) is tris(2-hexyldecyl)aluminum.

* * * * *

UNITED STATES PATENT AND TRADEMARK OFFICE
CERTIFICATE OF CORRECTION

PATENT NO. : 5,847,177
DATED : December 8, 1998
INVENTOR(S) : Samuel A. Sangokoya and Karl E. Wiegand It is certified that error appears in the above-identified patent and that said Letters Patent is hereby corrected as shown below:

| | |
|---|---|
| Column 1, Line 59 reads | "malt" |
| Should read | -- may -- |
| Column 3, Line 65 reads | "10g" |
| Should Read | -- 100g -- |
| Column 4, Line 46 reads | "salvation" |
| Should read | -- solvation -- |
| Column 5, Line 29 reads | "agitated hydrocarbon medium" |
| Should read | --agitated -- |

Signed and Sealed this

Eleventh Day of May, 1999

Attest:

Q. TODD DICKINSON

Attesting Officer     Acting Commissioner of Patents and Trademarks